United States Patent
Beaupre

(10) Patent No.: US 10,989,643 B2
(45) Date of Patent: Apr. 27, 2021

(54) METHOD FOR DETERMINING DENSITY OF FRESH CONCRETE, COMPUTING DEVICE AND SYSTEM THEREFORE

(71) Applicant: Command Alkon Incorporated, Birmingham, AL (US)

(72) Inventor: Denis Beaupre, Québec (CA)

(73) Assignee: Command Alkon Incorporated, Birmingham, AL (US)

( * ) Notice: Subject to any disclaimer, the term of this patent is extended or adjusted under 35 U.S.C. 154(b) by 135 days.

(21) Appl. No.: 16/311,281

(22) PCT Filed: Jul. 4, 2017

(86) PCT No.: PCT/EP2017/066658
§ 371 (c)(1),
(2) Date: Dec. 19, 2018

(87) PCT Pub. No.: WO2018/007396
PCT Pub. Date: Jan. 11, 2018

(65) Prior Publication Data
US 2019/0204197 A1    Jul. 4, 2019

Related U.S. Application Data

(60) Provisional application No. 62/358,405, filed on Jul. 5, 2016.

(51) Int. Cl.
*G01N 9/24* (2006.01)
*G01N 29/024* (2006.01)
(Continued)

(52) U.S. Cl.
CPC ............ *G01N 9/24* (2013.01); *G01N 29/00* (2013.01); *G01N 29/024* (2013.01);
(Continued)

(58) Field of Classification Search
CPC .... G01N 33/383; G01N 29/02; G01N 29/024; G01N 29/222; G01N 29/4418;
(Continued)

(56) References Cited

U.S. PATENT DOCUMENTS

| 4,522,068 A | * | 6/1985 | Smith | ...................... G01N 9/24 |
| | | | | 73/32 A |
| 5,412,990 A | * | 5/1995 | D'Angelo | ................ G01H 5/00 |
| | | | | 374/53 |

(Continued)

FOREIGN PATENT DOCUMENTS

| EP | 2545352 A2 | 1/2013 |
| JP | 2013529288 A | 7/2013 |
| WO | WO-2013152302 A1 | 10/2013 |

OTHER PUBLICATIONS

Requisition by the Examiner issued for Canadian Patent Application No. 3,028,866, dated Jul. 13, 2020, 5 pages.
(Continued)

*Primary Examiner* — Helen C Kwok
(74) *Attorney, Agent, or Firm* — Norton Rose Fulbright US LLP

(57) ABSTRACT

There is disclosed a computer-implemented method for determining a density value of a fresh concrete sample using an acoustic probe assembly. The acoustic probe assembly has an acoustic path, an acoustic emitter configured to emit an acoustic signal along the acoustic path, and an acoustic receiver configured to receive the acoustic signal after propagation along the acoustic path. The acoustic probe assembly is configured and adapted to generate an electromagnetic signal indicative of a duration of time taken by the acoustic signal to travel from the acoustic emitter to the acoustic receiver across the fresh concrete sample. The method generally has a step of determining the duration of time based on the electromagnetic signal, a step of matching
(Continued)

the duration to a density value using reference data, and a step of displaying the density value.

22 Claims, 6 Drawing Sheets

(51) Int. Cl.
    *G01N 29/22*       (2006.01)
    *G01N 29/44*       (2006.01)
    *G01N 33/38*       (2006.01)
    *G01N 29/00*       (2006.01)

(52) U.S. Cl.
    CPC ....... *G01N 29/222* (2013.01); *G01N 29/4418* (2013.01); *G01N 29/4427* (2013.01); *G01N 33/383* (2013.01); *G01N 2291/011* (2013.01); *G01N 2291/02416* (2013.01); *G01N 2291/02818* (2013.01); *G01N 2291/048* (2013.01); *G01N 2291/102* (2013.01)

(58) Field of Classification Search
    CPC ........ G01N 29/4427; G01N 9/24; G01N 9/26; G01N 9/08; G01N 9/10; G01N 9/14
    See application file for complete search history.

(56) References Cited

U.S. PATENT DOCUMENTS

| | | | | |
|---|---|---|---|---|
| 5,992,223 A | * | 11/1999 | Sabins | ................. G01N 29/032 73/54.03 |
| 6,227,039 B1 | * | 5/2001 | Te'eni | ................. C04B 40/0032 73/54.03 |
| 2009/0112365 A1 | * | 4/2009 | Orr | ................... B01F 15/00207 700/269 |
| 2013/0192351 A1 | * | 8/2013 | Fernald | ................. G01F 1/7082 73/61.49 |
| 2014/0297204 A1 | * | 10/2014 | Biesak | ............... G01N 29/4472 702/56 |
| 2015/0142362 A1 | * | 5/2015 | Jordan | ...................... B01F 9/06 702/96 |
| 2016/0025700 A1 | * | 1/2016 | Beaupre | ................. B28C 5/422 73/433 |
| 2016/0187266 A1 | * | 6/2016 | Annan | ................... G01N 22/04 324/640 |
| 2017/0217047 A1 | * | 8/2017 | Leon | .................... G01N 33/383 |

OTHER PUBLICATIONS

Robeyet, N. et al. "Monitoring the Setting of Concrete Containing Blast-furnace Slag by Measuring the Ultrasonic P-wave Velocity" Cement and Concrete Research, vol. 38, No. 10, Oct. 2008, 8 pages.
Second Written Opinion of the International Preliminary Examining Authority issued for PCT Application No. PCT/EP2017/066658, dated Oct. 16. 2018, 8 pages.
T. Hirschi et al., "Sika Concrete Handbook", Dec. 1, 2005; Switzerland; 151 pages.
International Search Report and Written Opinion issued for PCT Application No. PCT/EP2017/066658, dated Dec. 10, 2017; 15 pages.
Office Action dated Jan. 5, 2021 from Japanese Application No. 2019-521514, 10 pages. English Translation.

\* cited by examiner

METHOD FOR DETERMINING DENSITY OF FRESH CONCRETE, COMPUTING DEVICE AND SYSTEM THEREFORE

FIELD

The improvements generally relate to the handling of fresh concrete and more particularly to methods of determining a density of a sample thereof using acoustic methods.

BACKGROUND

Fresh concrete is formed of a mixture of ingredients including at least cement-based material and water in given proportions. The ingredients are typically transported inside a drum of a mixer truck where the fresh concrete can be mixed prior to pouring thereof.

It is known that density of the fresh concrete is indicative of the compressive strength the concrete will have once it has hardened.

International patent application number WO 2014/138, 968 describes a method of determining the density of fresh concrete of a mixer truck by measuring a buoyancy of a sensor immersed into the fresh concrete. Although existing methods were satisfactory to a certain extent, there remains room for improvement, especially when the fresh concrete has a low workability which prevents the sensor to float freely.

SUMMARY

The present disclosure describes a computer-implemented method of determine density of a fresh concrete sample based on a measurement of the amount of time taken by an acoustic signal to travel a given distance within the fresh concrete and also using reference data associated with the known recipe of the fresh concrete sample being analyzed. In some embodiments, the composition of the fresh concrete sample is received, and the reference data are selected, based on the received composition, among a plurality of reference data pertaining to a plurality of fresh concrete samples.

In accordance with one aspect, there is provided a system comprising: an acoustic probe assembly mounted to a concrete mixer, the acoustic probe assembly having an acoustic path, an acoustic emitter configured to emit an acoustic signal along the acoustic path, and an acoustic receiver configured to receive the acoustic signal after propagation along the acoustic path, the acoustic probe assembly being configured and adapted to generate an electromagnetic signal indicative of a duration of time taken by the acoustic signal to travel from the acoustic emitter to the acoustic receiver across a fresh concrete sample handled by the concrete mixer; a computing device communicatively coupled with the acoustic probe assembly, the computing device being configured for performing the steps of determining the duration of time based on the electromagnetic signal; and matching the duration of time to a density value using reference data; and a user interface communicatively coupled with the computing device, the user interface being configured to display the density value of the fresh concrete sample.

In accordance with another aspect, there is provided a computer-implemented method for determining a density value, the method comprising: receiving an electromagnetic signal indicative of a duration of time taken by an acoustic signal to travel from an acoustic emitter to an acoustic receiver across a fresh concrete sample handled by a fresh concrete mixer; determining the duration of time based on the electromagnetic signal; and matching the duration of time to a density value using reference data, and displaying the density value.

In accordance with another aspect, there is provided a computing device for determining a density value, the computing device comprising: a memory having stored thereon program code executable by a processor; and at least one processor configured for executing the program code, the memory and the at least one processor being configured for performing the steps of the computer-implemented method as described above.

In accordance with another aspect, there is provided a computer-implemented method comprising: receiving an electromagnetic signal indicative of a duration of time taken by an acoustic signal to travel from an acoustic emitter to an acoustic receiver across a fresh concrete sample handled by a fresh concrete mixer; determining the duration of time based on the electromagnetic signal; and comparing the duration to a duration threshold, and displaying that the density value is one of above and below a density threshold when the duration is the one of above and below the duration threshold.

In accordance with another aspect, there is provided a computer-implemented method for producing reference data, the method comprising: receiving a reference duration of time taken by an acoustic signal to travel from an acoustic emitter to at least one acoustic receiver across a fresh concrete sample of a composition; receiving a reference density value indicative of a density of the fresh concrete sample; repeating said receiving steps for a plurality of fresh concrete samples of the same composition and of different air contents; and producing reference data for the composition of fresh concrete by associating the reference durations with the corresponding reference density values.

In accordance with another aspect, there is provided a system comprising: an acoustic probe assembly mounted to a stationary mixer of a concrete production plant, the acoustic probe assembly having an acoustic path, an acoustic emitter configured to emit an acoustic signal along the acoustic path, and an acoustic receiver configured to receive the acoustic signal after propagation along the acoustic path, the acoustic probe assembly being configured and adapted to generate an electromagnetic signal indicative of a duration of time taken by the acoustic signal to travel from the acoustic emitter to the acoustic receiver across a fresh concrete sample handled by the stationary mixer; a computing device communicatively coupled with the acoustic probe assembly, the computing device being configured for performing the steps of determining the duration of time based on the electromagnetic signal; and matching the duration of time to a density value using reference data; and a user interface communicatively coupled with the computing device, the user interface being configured to display the density value of the fresh concrete sample.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
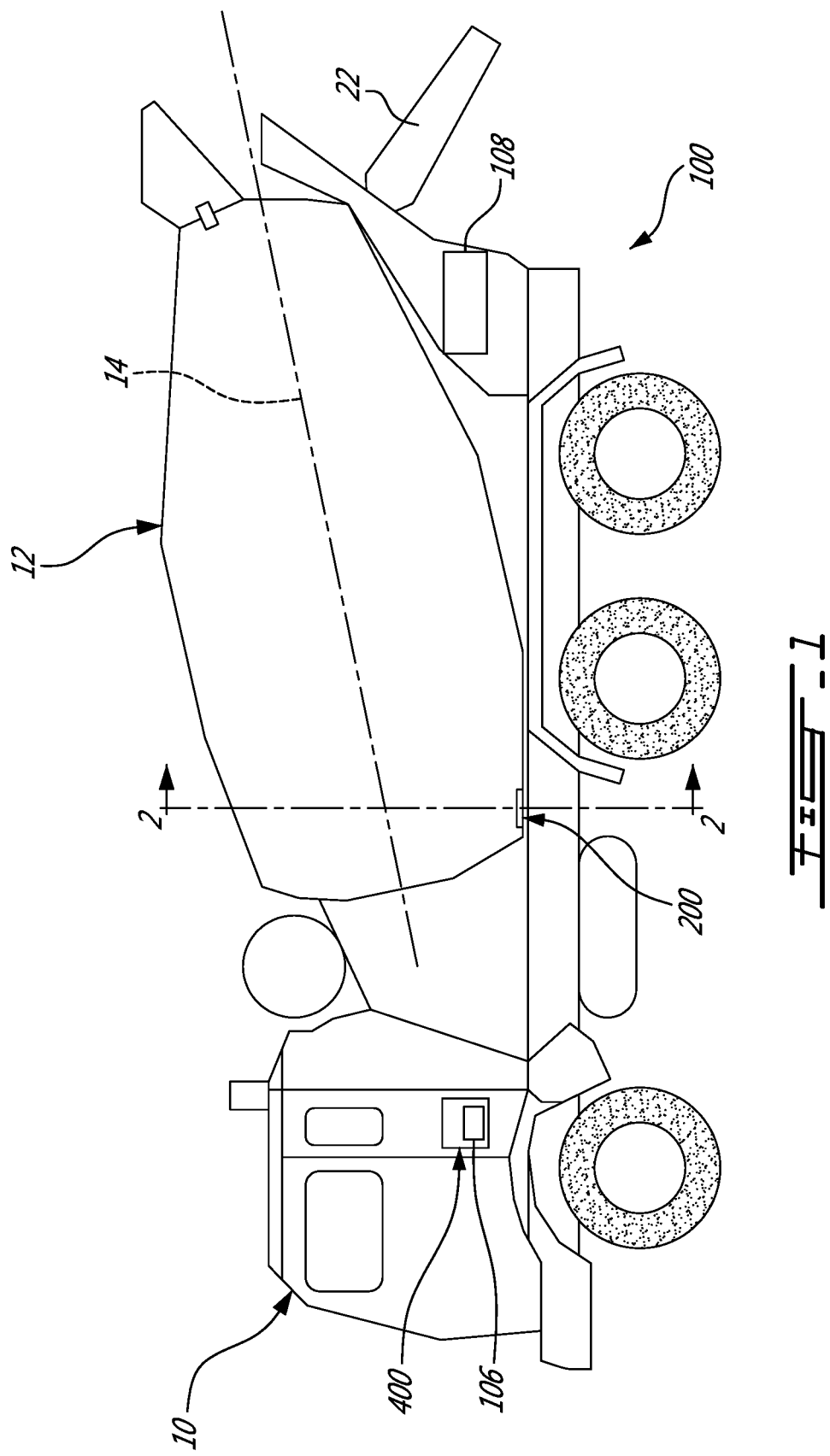
FIG. 1 is a schematic view of an example of a system for determining a density value of fresh concrete inside a drum of a mixer truck.

FIG. 1 shows an example of a concrete mixer used for handling of fresh concrete. As depicted, the concrete mixer is embodied in a mixer truck 10 having a drum 12 rotatable about a rotation axis 14 and a discharge chute 22 for discharging the fresh concrete. During use, the drum 12 of the mixer truck 10 is loaded with fresh concrete. The fresh concrete includes a cement-based material and water. A composition of the fresh concrete is given by the relative amount of cement-base material, water and other components. The fresh concrete is then mixed inside the drum 12 by rotating it about the rotation axis 14 until it is poured at a desired location for it to harden into a desired structure of a given compressive strength. The density of the fresh concrete can be used as an indication of the compressive strength once the fresh concrete has hardened.

A system 100 can be provided for determining the density value of the fresh concrete while it is being handled (e.g. mixed or poured), by the mixer truck 10. In the example illustrated, the system 100 includes an acoustic probe assembly 200 mounted inside the drum 12, a computing device 400 communicatively coupled (i.e. in a wired communication, a wireless communication, or both) with the acoustic probe assembly 200 using a wired connection, a wireless connection (e.g. Wifi™) or both. A user interface 106 is typically mounted to the mixer truck 10 and communicatively coupled with the computing device 400. The connection can be direct, or include a transmission across a network such as the Internet, for instance.

As shown in the figures, the concrete mixer receiving the acoustic probe assembly 200 can be in the form of a mixer truck. The acoustic probe assembly 200 can be mounted inside the drum 12 of the mixer truck 10 or, alternately, at any suitable location such as the discharge chute 22. In another embodiment, the acoustic probe assembly can be mounted to another form of concrete mixer, such as a stationary mixer of a concrete production plant.

In the illustrated embodiment, the computing device 400 is provided in the form of an on-board computer mounted to the mixer truck 10 and has the user interface 106 made integral thereto. In an alternate embodiment, the computing device 400 can be provided in the form of a remote computer, for instance, such as a hand-held device. The computing device 400 can communicate in a wired or in a wireless manner. In this example, the acoustic probe assembly 200 communicates with the computing device 400 via a communicator 108. The communicator 108 is mounted to the mixer truck 10 and can act as a receiver for receiving electromagnetic signal(s) generated by the acoustic probe assembly 200 and as a transmitter for transmitting the electromagnetic signal(s) to the computing device 400. The user interface 106 can be provided in the form of a display, a touch-sensitive display, LED lights, and/or any combination thereof. Any other suitable type of user interface can also be used.

Figure 2:
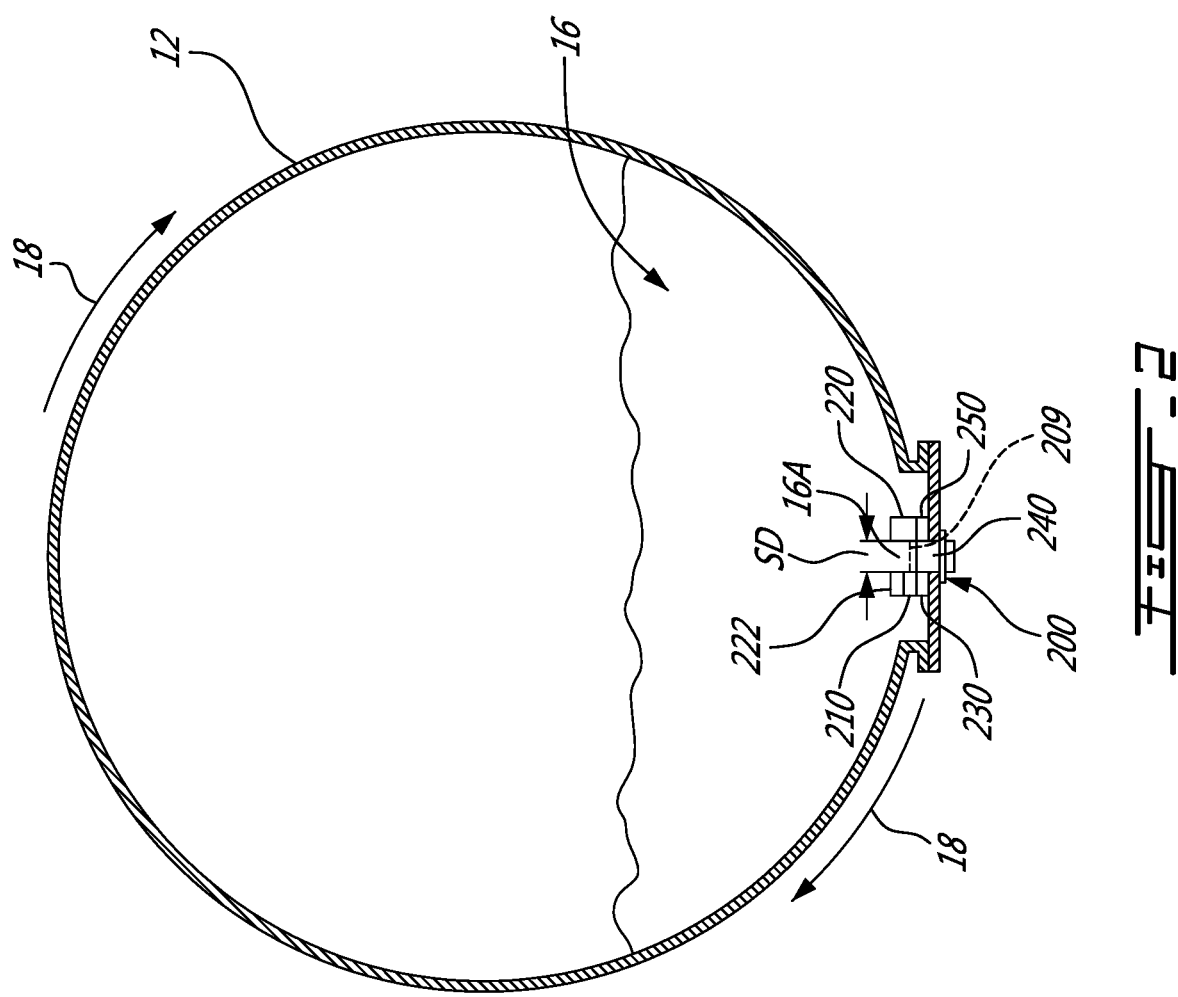
FIG. 2 is a sectional view taken along lines 2-2 of FIG. 1.

FIG. 2 shows a section of the drum 12 taken along lines 2-2 of FIG. 1. As illustrated, the drum 12 is loaded with fresh concrete 16 and rotated with respect to arrows 18. An example of the acoustic probe assembly 200 is shown. The acoustic probe assembly 200 has an acoustic path 209, an acoustic emitter 210 configured to emit an acoustic signal along the acoustic path 209, and at least one acoustic receiver, such as first acoustic receiver 220, configured to receive the acoustic signal after propagation along the acoustic path 209. As shown, the acoustic emitter 210 is spaced from the first acoustic receiver 220 by a spacing distance SD. In some embodiments, the spacing distance SD is 10 cm. The acoustic probe assembly 200 is configured and adapted to generate one or more electromagnetic signal(s) indicative of a duration of time (hereinafter "the duration $\Delta T$") taken by the acoustic signal to travel from the acoustic emitter 210 to the acoustic receiver 220 across a fresh concrete sample 16A handled by the concrete mixer.

In some embodiments, the acoustic probe assembly 200 can have a duration transmitter 230 for generating the duration $\Delta T$ in the form of electromagnetic signal(s) (e.g., digital signal(s) and/or analog signal(s)) to the communicator 108 shown in FIG. 1. In some embodiments, the duration transmitter 230 is configured to transmit the duration $\Delta T$ directly to the computing device 400 as shown in FIG. 1, in which case the computing device 400 determines the duration $\Delta T$ by receiving it.

In some other embodiments, the electromagnetic signal(s) generated by the acoustic probe assembly 200 can indicate when the acoustic signal is emitted by the acoustic emitter 210 and when the acoustic signal is received by the first acoustic receiver 220 so that the computing device 400 can determine the duration $\Delta T$ by calculating it from the electromagnetic signal(s). In these embodiments, for instance, the first acoustic receiver 220 can include a second acoustic receiver 222 adjacent to the acoustic emitter 210 and opposed to the first acoustic receiver 220 to detect when the acoustic signal is emitted. The second acoustic receiver 222 generates a first electromagnetic signal when it receives the acoustic signal emitted by the acoustic emitter 210, and the first acoustic receiver 220 generates a second electromagnetic signal when it receives the acoustic signal emitted by the acoustic emitter 210, after propagation along the acoustic path 209. In this embodiment, the duration $\Delta T$ is determined by calculating a difference between the moment in time t2 at which time the first electromagnetic signal is received and the moment in time t1 at which time the second electromagnetic signal is received, i.e. $\Delta T = t2 - t1$.

Any type of acoustic probe assembly can be used. For instance, the acoustic probe assembly 200 shown in the figure is in a transmission configuration. In alternate embodiments, the acoustic probe assembly can be configured into a reflection configuration wherein the acoustic emitter and the acoustic receiver are both oriented towards an acoustic reflector (not shown). In this case, the spacing distance is based on the distance between the acoustic transmitter and the acoustic reflector, and on the distance between the acoustic reflector and the acoustic receiver. Other variations are possible. The acoustic signal can be any suitable type of acoustic signal (e.g., pulsed, frequency chirped, high frequency).

As depicted, the acoustic probe assembly 200 has a position sensor 240 (e.g., an accelerometer) configured to generate position data indicative of the position of the acoustic probe assembly 200 relative to the mixer truck 10 over time. For instance, the duration $\Delta T$ can be determined when the acoustic probe assembly 200 is at its lower position (the position shown in FIG. 2) such that the acoustic emitter 210 and the first acoustic receiver 220 are immersed in the fresh concrete 16.

The acoustic probe assembly 200 can be powered by a rechargeable power source 250. Any suitable type of rechargeable power source can be provided. For instance, the rechargeable power source can include batteries and can be charged via a power cord, solar panel(s), an induction process, or any other suitable charging means.

Figure 3:
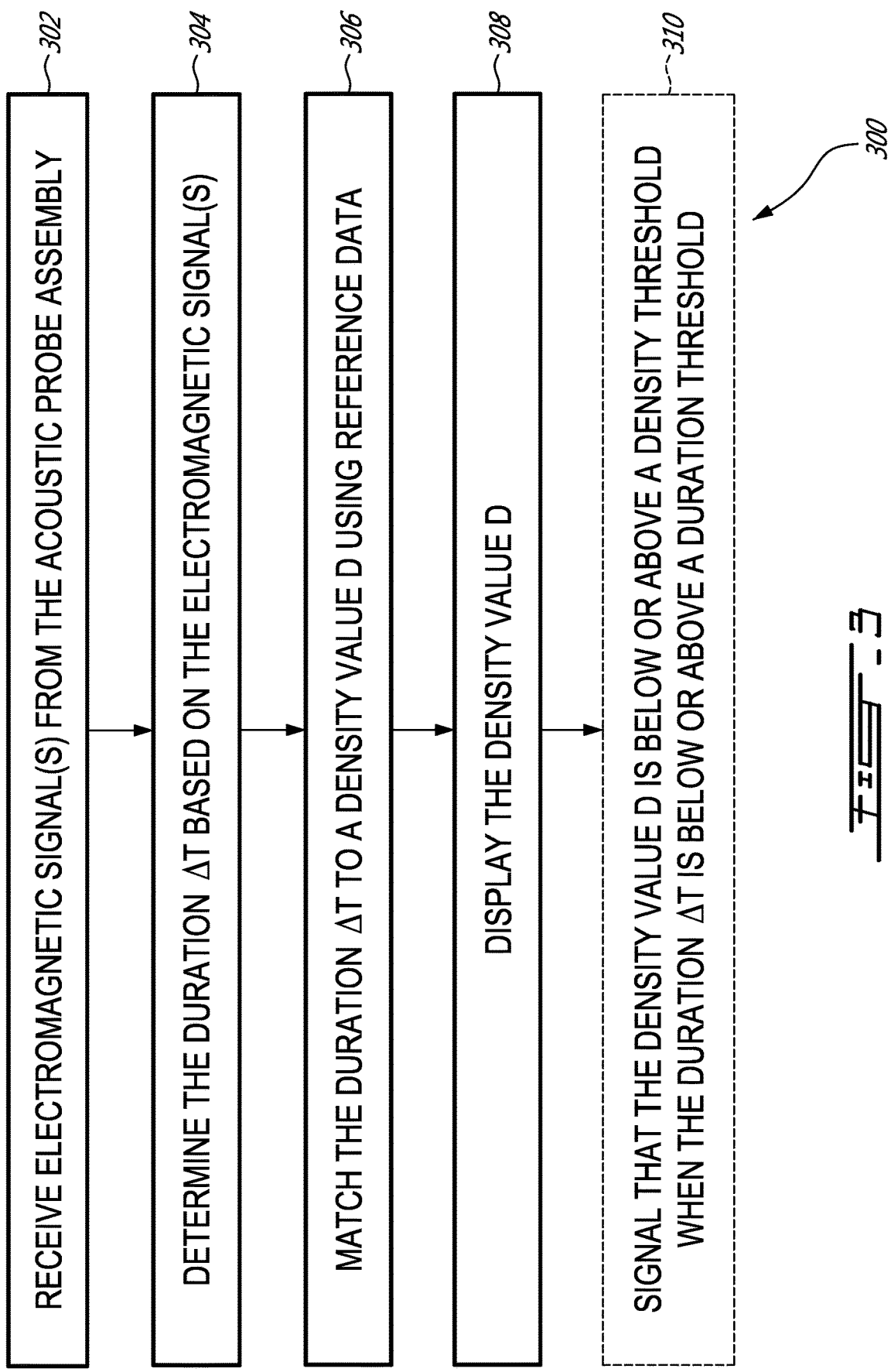
FIG. 3 is a flow chart of an example method for determining a density value of fresh concrete inside the drum of the mixer truck of FIG. 1.

FIG. 3 shows a flowchart of a computer-implemented method 300 for determining a density value D. As the method 300 can be performed by the computing device 400, reference to FIGS. 1 and 2 will be made in the following paragraphs. In this context, the density value D is indicative of the density of the fresh concrete sample 16A.

As per step 302, the electromagnetic signal(s) generated by the acoustic probe assembly 200 is(are) received. The electromagnetic signal(s) is(are) indicative of the duration $\Delta T$ taken by the acoustic signal to travel from the acoustic emitter 210 to the first acoustic receiver 220 along the acoustic path 209 and across the fresh concrete sample 16A.

As per step 304, the duration $\Delta T$ is determined based on the electromagnetic signal(s). As mentioned above, the duration $\Delta T$ can either be received directly from the electromagnetic signal(s) or calculated from the electromagnetic signal(s).

As per step 306, the duration $\Delta T$ is matched to a density value D using reference data. The reference data can be obtained previously to the determination of the duration $\Delta T$. The reference data can be obtained from measurements previously made on a fresh concrete sample having the same composition as the composition of the fresh concrete sample 16A.

The reference data include reference durations $\Delta T_{ref,i}$ indicative of a duration required for an acoustic signal to travel from an acoustic emitter (e.g., the acoustic emitter 210) to an acoustic receiver (e.g., the first acoustic receiver 220) across the fresh concrete sample. The reference data also include reference density values $D_{ref,i}$ indicative of a density of the fresh concrete sample. Each reference density $D_{ref,i}$ value has reference duration associated thereto $\Delta T_{ref,i}$.

The reference data can be provided in the form of a lookup table or a mathematical relationship associating reference durations to corresponding reference density values. The reference data is stored in a computer-readable memory accessible by a processor, and can include stored values and stored software instructions.

In the case of the lookup table, for instance, the step 306 of matching can include a step of looking up the reference data to find a given reference duration $\Delta T_{ref,i}$ corresponding to the duration $\Delta T$ and a subsequent step of determining that the density value D corresponds to a reference density $D_{ref,i}$ value associated with the given reference duration $\Delta T_{ref,i}$. In this example, the variable i is an integer indicative of the index of the given duration in the lookup table.

In some embodiments, a step of extrapolating the density value D using the reference data can be performed. For instance, the step of looking up the reference data can include a step of finding two reference durations $\Delta T_{ref,j}$, $\Delta T_{ref,j+1}$ surrounding the duration $\Delta T$ (i.e. $\Delta T_{ref,j} < \Delta T < \Delta T_{ref,j+1}$), and a step of extrapolating the density value D based on at least two reference density values $D_j$, $D_j$ associated with the two reference durations $\Delta T_{ref,j}$, $\Delta T_{ref,j+1}$. In this example, the variable j is an integer indicative of the index of the given duration in the lookup table.

For instance, Table 1 shows reference data T1 associated with a given composition C1 of a fresh concrete sample, and provided in the form of a lookup table. In this case, the composition C1 includes a water cement ("w/c") ratio of 0.5. The differing densities of the fresh concrete of a same composition may be due to differing air contents, for instance. It will be noted that this table has been simplified and is provided as a visual support to explain a possible embodiment.

| T1 | | |
|---|---|---|
| i | $\Delta T_{ref,i}$ [ms] | $D_{ref,i}$ [kg/m$^3$] |
| 1 | 0.60 | 2140 |
| 2 | 0.65 | 2175 |
| 3 | 0.70 | 2210 |
| 4 | 0.75 | 2250 |

Table 1 shows reference data T1 for a given composition C1 of a fresh concrete sample In this case, the density value can be determined based on the lookup table. For instance, the calculation of the density value can include finding two (or more) reference durations surrounding the duration $\Delta T$ and extrapolating the density value based on two (or more) reference density values associated with the two reference durations. For instance, for the composition C1, if the duration $\Delta T$ is 0.625 ms, the density value can be extrapolated using the couples (0.60 ms, 2140 kg/m$^3$) and (0.65 ms, 2175 kg/m$^3$). In another example, the lookup table can be more exhaustive and the determination of the density value can be based on a nearest match of a corresponding value of the table, for instance.

Reference data can be provided for more than one composition of fresh concrete. For instance, reference data can be provided for composition of fresh concrete having any acceptable w/c ratio. Reference data can also be provided for composition of fresh concrete including one or more admixtures.

The determination of the density value can be based on a calculation based on a mathematical relationship between duration and density. In the case of the mathematical equation, the step 306 of matching can include inputting the duration $\Delta T$ into the software instructions executing the calculation in accordance with a given mathematical relationship, and determining that the density value corresponds to a result of said inputting. For instance, the mathematical relationship can output the density value D based on the duration $\Delta T$, i.e. $D = f(\Delta T)$.

In some embodiments, the mathematical relationship can stem from a curve fitting using experimental data. For instance, with a linear curve fitting, the reference data T1 of the given composition C1 can be approximated to the mathematical equation $D = 730000 \cdot \Delta T + 1701$. Curve fitting types other than linear can be used depending of the reference data. For instance, fitting can be performed using polynomial functions. A curve fitting algorithm can be used to provide such a mathematical equation based on reference data.

As per step 308, the density value D is displayed. In some embodiments, the density value D can be displayed on the user interface 106 shown in FIG. 1.

As per optional step 310, a comparison between the duration $\Delta T$ and a duration threshold $\Delta T_{thres}$ can be made. In this case, the density value D being below or above a density threshold $D_{thres}$ when the duration $\Delta T$ is below or above the duration threshold $\Delta T_{thres}$ can be signaled.

In some embodiments, the user interface 106 can include a green LED, a yellow LED and a red LED. In these embodiments, the green LED can be activated as long as the density value D is above the density threshold $D_{thres}$, the yellow LED can be activated when the density value D corresponds to the density threshold $D_{thres}$, and the red LED can be activated when the density value D is below the density threshold $D_{thres}$. Different types of sounds can be substituted or added to any of the LED lights. For instance, a sound alarm can be activated when density value D is below the density threshold $D_{thres}$.

As it will be understood, the density threshold $D_{thres}$ can be associated with a minimal (or maximal) compressive strength. For instance, if the density value D of the fresh concrete sample 16A is below the minimum density threshold $D_{thres}$, the compressive strength of the fresh concrete, when hardened, can be below the minimal compressive strength. The signal can be to avoid pouring the fresh concrete, as its density is not acceptable.

As mentioned above, the reference data depend on the composition of the fresh concrete sample. In some embodiments, the method 300 is adapted to be used for only one composition and thus the reference data remain the same throughout the steps of the method 300.

In some embodiments, the reference data used in the method 300 are selected from a plurality of reference data pertaining to a plurality of different compositions of fresh concrete samples in accordance with the composition of the fresh concrete sample in the drum of the mixer truck. The composition of such fresh concrete sample can be obtained from an input (e.g., user interface 106 shown in FIG. 1).

For example, reference data $(\Delta T_{ref,C1}, D_{ref,C1})$, $(\Delta T_{ref,C2}, D_{ref,C2})$ and $(\Delta T_{ref,C3}, D_{ref,C3})$ associated with three different compositions C1, C2 and C3, respectively, can be obtained. In this case, if the composition that is received from the input indicates that the composition of the fresh concrete sample is composition C3, then reference data $(\Delta T_{ref,C3}, D_{ref,C3})$ are selected from all the other reference data, and then the matching of the duration $\Delta T$ to the density value D, as per step 306, is based on the selected reference data $(\Delta T_{ref,C3}, D_{ref,C3})$.

In some embodiments, the reference data can include reference air content data $AC_{ref}$ indicative of a reference air content of the fresh concrete sample. In this case, the method 300 can have a step of determining air content data AC indicative of the air content of the fresh concrete sample based on the determined density value D and on the reference air content data $AC_{ref}$. For instance, determining the air content data AC includes calculating the addition of the reference air content data $AC_{ref}$ to a ratio of a difference between the reference density value and the determined density value over the reference density value following equation (1):

$$AC=AC_{ref}+(D_{ref}-D)/(D_{ref}). \qquad (1)$$

Accordingly, if the determined density value D is equal to the reference density value $D_{ref}$, the air content data AC correspond to the reference air content data $AC_{ref}$. If the determined density value D is lower than the reference density value $D_{ref}$, the air content data AC correspond to the addition of the reference air content data $AC_{ref}$ to the ratio $(D_{ref}-D)/(D_{ref})$. If the determined density value D is greater than the reference density value $D_{ref}$, the air content data AC correspond to the subtraction between the reference air content data $AC_{ref}$ and the ratio $(D-D_{ref})/(D_{ref})$.

A computer-implemented method for producing such reference data is also provided. The method has a step of receiving a reference duration $\Delta T_{ref,1}$ of time taken by an acoustic signal to travel from an acoustic emitter to an acoustic receiver across a fresh concrete sample of a composition. The method has a step of receiving a reference density value $D_{ref,1}$ indicative of a density of the fresh concrete sample. The method has a step of repeating said receiving steps for a plurality of fresh concrete samples of the same composition but, for instance, of different air contents. The method has a step of producing the reference data $(\Delta T_{ref}, D_{ref})$ for the composition of fresh concrete by associating the reference durations with the corresponding reference density values. This method of producing reference data can be performed to produce reference associated with another composition of fresh concrete in order to provide, for instance, a plurality of reference data pertaining to a plurality of different compositions of fresh concrete samples.

Figure 4:
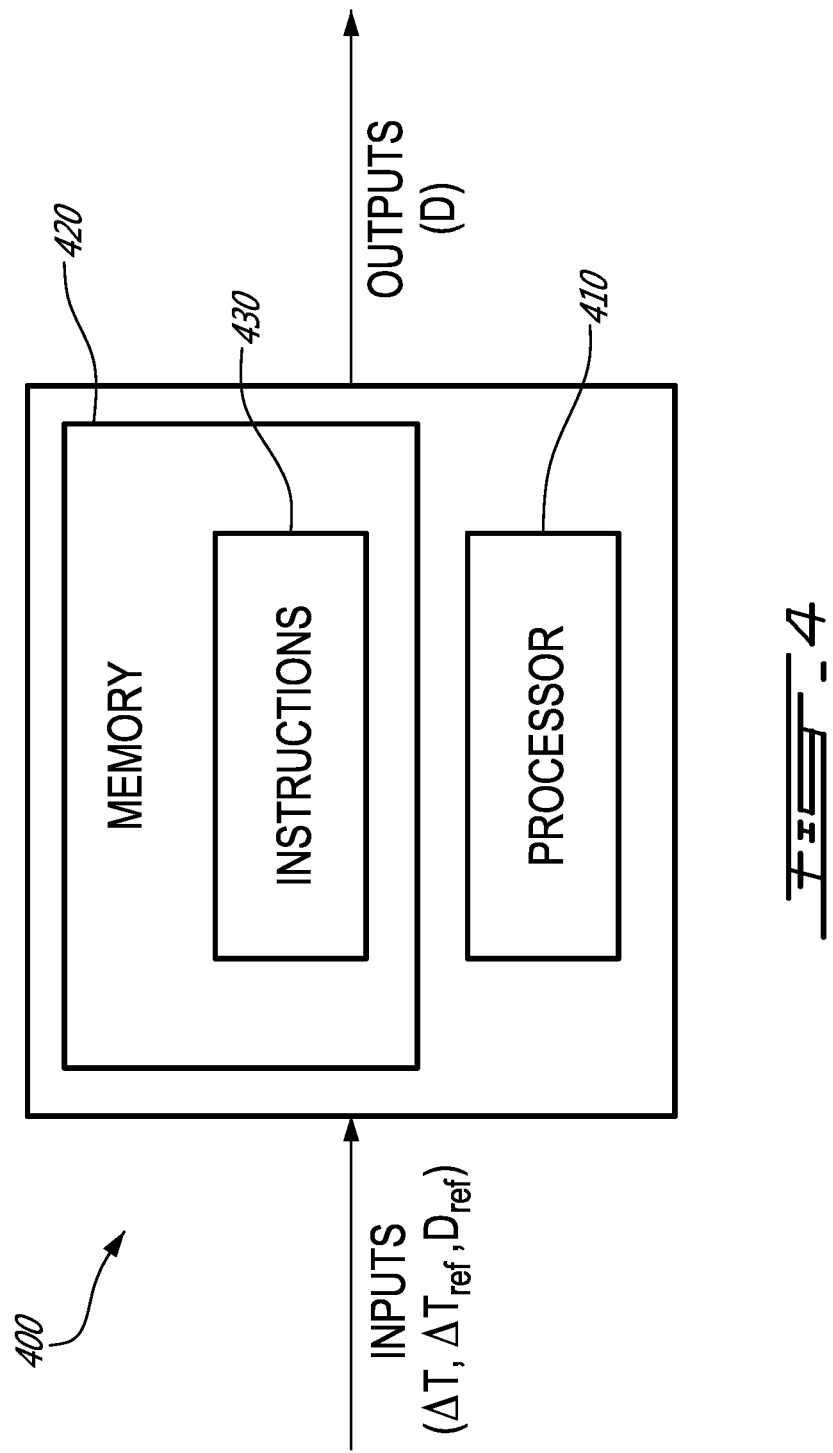
FIG. 4 is a block diagram of an example software and hardware implementations of the example method of FIG. 3.

FIG. 4 shows a schematic representation of an example implementation of the method 300 as a combination of software and hardware components. The computing device 400 is illustrated with one or more processors (referred to as "the processor 410") and one or more computer-readable memories (referred to as "the memory 420") having stored thereon program instructions 430 configured to cause the processor 410 to generate one or more outputs based on one or more inputs. The inputs can comprise one or more signals representative of the duration $\Delta T$ and reference data $(\Delta T_{ref}, D_{ref})$. The outputs can comprise one or more signals representative of the density value D, a signal that the density value D is lower than a minimum density threshold $D_{min}$.

The processor 410 can comprise any suitable devices configured to cause a series of steps to be performed so as to implement the computer-implemented method 300 such that instructions 430, when executed by the computing device 400 or other programmable apparatus, can cause functions/acts/steps specified in the methods described herein to be executed. The processor 410 can comprise, for example, any type of general-purpose microprocessor or microcontroller, a digital signal processing (DSP) processor, a central processing unit (CPU), an integrated circuit, a field programmable data array (FPGA), a reconfigurable processor, other suitably programmed or programmable logic circuits, or any combination thereof.

The memory 420 can comprise any suitable known or other machine-readable storage medium. The memory 420 can comprise non-transitory computer readable storage medium such as, for example, but not limited to, an electronic, magnetic, optical, electromagnetic, infrared, or semiconductor system, apparatus, or device, or any suitable combination of the foregoing. The memory 420 can include a suitable combination of any type of computer memory that is located either internally or externally to devices such as, for example, random-access memory (RAM) read-only memory (ROM), compact disc read-only memory (CDROM), electro-optical memory, magneto-optical memory, erasable programmable read-only memory (EPROM), and electrically-erasable programmable read-only memory (EEPROM), ferroelectric RAM (FRAM) or the like. Memory 420 can comprise any storage means (e.g., devices) suitable for retrievably storing machine-readable instructions executable by the processor 410.

Figure 5:
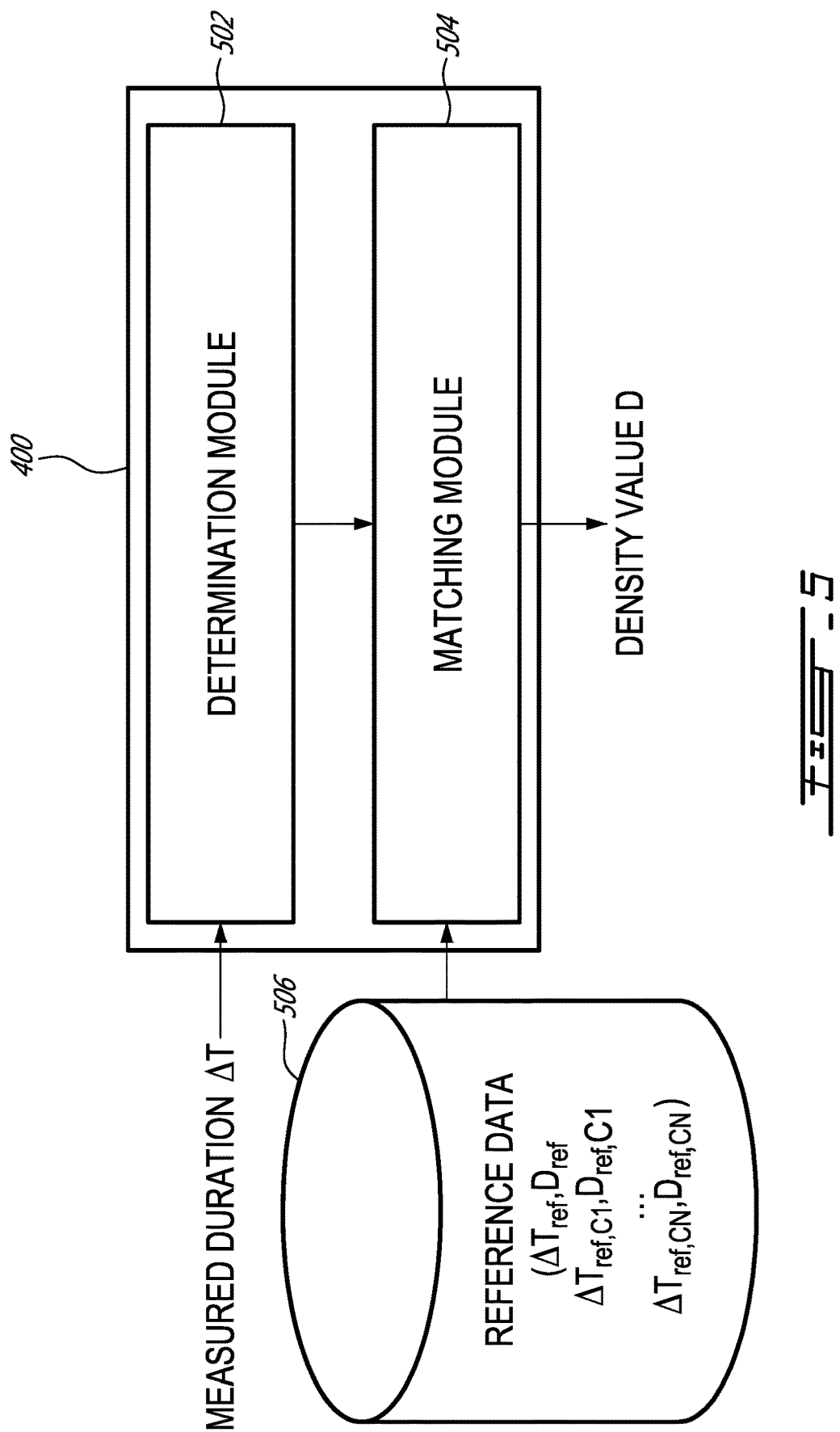
FIG. 5 is a block diagram of an example of a computing device.

FIG. 5 is a block diagram of an exemplary embodiment of the computing device 400, which can be implemented by the processor 410. As depicted, a determination module 502 and a matching module 504 embody the instructions 430 shown in FIG. 4.

The determination module 502 is configured to receive the electromagnetic signal(s) from the acoustic probe assembly and to determine the duration $\Delta T$ based on the electromagnetic signal(s), as per steps 302 and 304. The determination module 502 can be in communication with the acoustic probe assembly 200 to receive the electromagnetic signal(s) and, directly or indirectly, the duration ΔT therefrom. The duration ΔT, once determined, is provided to the matching module 504.

The matching module 504 is configured to obtain the reference data and to match the duration ΔT to a density value D using the reference data, as per step 306. The matching module 504 can be coupled with a database 506 on which is stored the reference data (ΔT$_{ref}$, D$_{ref}$, AC$_{ref}$, or mathematical relation D=f(ΔT)) for one or more compositions C1, . . . , or C$_N$ of fresh concrete. The database 506 can be provided locally to the computing device 400, or remotely therefrom. In some embodiments, the database 506 corresponds to the memory 420 of the computing device 400.

Once determined, the density value D can be displayed on a user interface and/or stored on the database 506. Previously stored density value can form history data representative of the evolution of the density over time.

The matching module 504 can also be configured to signal that the density value is below or above a density threshold D$_{thres}$ when the duration ΔT is below or above the duration threshold ΔT$_{thres}$.

The database 506 can be provided in the form of a single database accessible by the determination module 502 and the matching module 504. Although shown as separate from the computing device 400, the database 506 can be integrated therewith.

Figure 6:
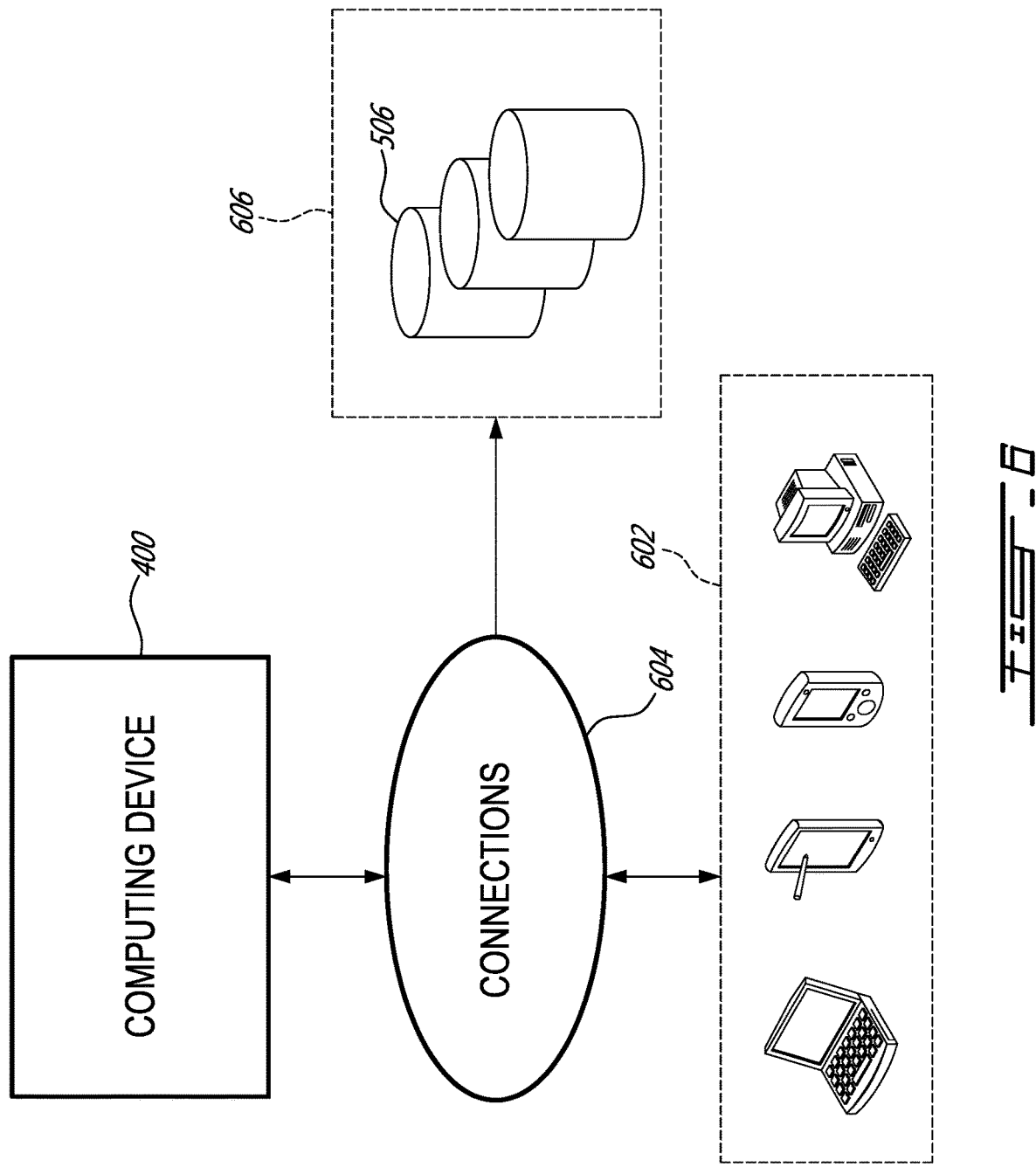
FIG. 6 is a diagram illustrating an example system for determining a density value.

Referring now to FIG. 6, in some embodiments, the computing device 400 can be accessible remotely from any one of a plurality of external devices 602 over connections 604. External devices 602 can have an application, or a combination thereof, for accessing the computing device 400. Alternatively, external devices 602 can access the computing device 400 via a web application, accessible through any type of Web browser.

The connections 604 can comprise wire-based technology, such as electrical wires or cables, and/or optical fibers. The connections 604 can also be wireless, such as RF, infrared, Wi-Fi, Bluetooth, and others. The connections 604 can therefore comprise a network, or others known to those skilled in the art. Communication over the network can occur using any known protocols that enable external devices 602 within a computer network to exchange information. The examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), or SSH (Secure Shell Remote Protocol).

In some embodiments, the computing device 400 is provided at least in part on any one of external devices 602. For example, the computing device 400 can be configured as a first portion provided in the system 100 to obtain and transmit the duration ΔT to a second portion, provided on one of the external devices 602. The second portion can be configured to receive the inputs ΔT, ΔT$_{ref}$ and/or D$_{ref}$ and perform any one of steps 306, 308 on one of the external devices 602. Alternatively, computing device 400 is provided entirely on any one of the external devices 602 and is configured to receive from a user inputs ΔT, ΔT$_{ref}$ and/or D$_{ref}$. Also alternatively, the system 100 is configured to transmit, via connections 604, one or more of inputs ΔT, ΔT$_{ref}$ and/or D$_{ref}$. Other embodiments may also apply.

One or more databases 606, such as database 506 can be provided locally on any one of the computing device 400 and the external devices 602, or can be provided separately therefrom (as illustrated). In the case of a remote access to the databases 606, access can occur via the connections 604 taking the form of any type of network, as indicated above. The various databases 606 described herein can be provided as collections of data or information organized for rapid search and retrieval by a computer. The databases 606 can be structured to facilitate storage, retrieval, modification, and deletion of data on a data storage medium, such as one or more servers. The databases 606 illustratively have stored therein raw data representing a plurality of features of the system 100, the features being, for example, a mathematical relation between the duration ΔT and the density value D.

Each computer program described herein can be implemented in a high level procedural or object oriented programming or scripting language, or a combination thereof, to communicate with a computer system. Alternatively, the programs can be implemented in assembly or machine language. The language can be a compiled or interpreted language. Computer-executable instructions can be in many forms, including program modules, executed by one or more computers or other devices. Generally, program modules include routines, programs, objects, components, data structures, etc., that perform particular tasks or implement particular abstract data types. Typically the functionality of the program modules can be combined or distributed as desired in various embodiments.

As can be understood, the examples described above and illustrated are intended to be exemplary only. Various aspects of the present computing device 400 can be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment can be combined in any manner with aspects described in other embodiments. Although particular embodiments have been shown and described, it will be obvious to those skilled in the art that changes and modifications can be made without departing from this invention in its broader aspects. The scope is indicated by the appended claims.

What is claimed is:

1. A system comprising:
    an acoustic probe assembly mounted to a concrete mixer, the acoustic probe assembly having an acoustic path, an acoustic emitter configured to emit an acoustic signal along the acoustic path, and an acoustic receiver configured to receive the acoustic signal after propagation along the acoustic path, the acoustic probe assembly being configured and adapted to generate an electromagnetic signal indicative of a duration of time taken by the acoustic signal to travel from the acoustic emitter to the acoustic receiver across a fresh concrete sample handled by the concrete mixer;
    a computing device communicatively coupled with the acoustic probe assembly, the computing device being configured for performing the steps of
    receiving composition data indicative of a composition of the fresh concrete sample;
    determining the duration of time based on the electromagnetic signal; and
    matching the duration of time to a density value using reference data pertaining to the received composition data; and a user interface communicatively coupled with the computing device, the user interface being configured to display the density value of the fresh concrete sample.

2. The system of claim 1 wherein the acoustic probe assembly includes a duration of time transmitter for transmitting the duration to the computing device.

3. The system of claim 1 wherein the acoustic probe assembly has at least one accelerometer for generating position data indicative of a position of the acoustic probe assembly relatively to the concrete mixer.

4. The system of claim 1 wherein the acoustic probe assembly is mounted inside a drum of the concrete mixer.

5. The system of claim 1 wherein the acoustic receiver is a first acoustic receiver, the acoustic probe assembly including a second acoustic receiver adjacent to the acoustic emitter and opposed to the first acoustic receiver to detect when the acoustic signal is emitted.

6. A computer-implemented method for determining a density value, the method comprising:
receiving an electromagnetic signal indicative of a duration of time taken by an acoustic signal to travel from an acoustic emitter to an acoustic receiver across a fresh concrete sample handled by a fresh concrete mixer;
receiving composition data indicative of a composition of the fresh concrete sample;
determining the duration of time based on the electromagnetic signal; and
matching the duration of time to a density value using reference data pertaining to the received composition data, and displaying the density value.

7. The method of claim 6 wherein the reference data include a lookup table associating a plurality of reference durations with corresponding reference density values.

8. The method of claim 7 wherein said matching includes:
looking up the reference data to find a given reference duration corresponding to the duration of time; and
determining that the density value corresponds to a reference density value associated with the given reference duration.

9. The method of claim 8 wherein said looking up includes finding at least two reference durations surrounding the duration of time and extrapolating the density value based on at least two reference density values associated with the at least two reference durations.

10. The method of claim 6 wherein the reference data include a mathematical relation associating reference durations with corresponding reference density values.

11. The method of claim 10 wherein said matching includes:
inputting the duration of time into the mathematical relation; and
determining that the density value corresponds to a result of said inputting.

12. The method of claim 6 further comprising comparing the duration of time to a duration threshold, and wherein said electromagnetic signal is indicative that the density value is one of below and above a density threshold when the duration of time is the one of below and above the duration threshold.

13. The method of claim 6 wherein, prior to said matching, the method further comprises:
based on said received composition data, selecting the reference data associated with a composition of the fresh concrete sample among a plurality of reference data pertaining to a plurality of fresh concrete samples of different compositions;
wherein said matching uses the selected reference data.

14. The method of claim 13 wherein the composition data are received from an input.

15. The method of claim 6 wherein the reference data include reference air content data indicative of an air content of the fresh concrete sample, the method further comprising determining air content data based on the density value and on the reference air content data.

16. The method of claim 15 wherein said determining the air content data includes calculating the mathematical addition of the reference air content data to a ratio having a numerator corresponding to a difference between the reference density value and the density value, and a denominator corresponding to the reference density value.

17. A computing device for determining a density value, the computing device comprising:
a memory having stored thereon program code executable by a processor; and
at least one processor configured for executing the program code, the memory and the at least one processor being configured for performing the steps of the computer-implemented method of claim 6.

18. The computing device of claim 17 wherein the reference data have reference durations and corresponding reference density values for a plurality of fresh concrete samples of different compositions.

19. The computing device of claim 17 wherein the reference data include at least one of a lookup table and a mathematical relation associating reference durations with corresponding reference density values.

20. A computer-implemented method comprising:
receiving an electromagnetic signal indicative of a duration of time taken by an acoustic signal to travel from an acoustic emitter to an acoustic receiver across a fresh concrete sample handled by a fresh concrete mixer;
receiving composition data indicative of a composition of the fresh concrete sample;
determining the duration of time based on the electromagnetic signal; and
comparing the duration of time to a duration threshold pertaining to the received composition data, and displaying that a density value of said fresh concrete sample is one of above and below a density threshold when the duration of time is the one of above and below the duration threshold.

21. A computer-implemented method for producing reference data, the method comprising:
receiving a reference duration of time taken by an acoustic signal to travel from an acoustic emitter to at least one acoustic receiver across a fresh concrete sample of a composition;
receiving a reference density value indicative of a density of the fresh concrete sample;
repeating said receiving steps for a plurality of fresh concrete samples of the same composition and of different air contents thereby producing a plurality of reference durations of time; and
producing reference data for the composition of the fresh concrete by associating the plurality of reference durations of time with the corresponding reference density values and with composition data indicative of the composition of the fresh concrete sample.

22. The method of claim 21 further comprising performing said receiving, repeating and producing steps for at least another composition of the fresh concrete.

* * * * *